United States Patent [19]
Dunn et al.

[11] Patent Number: 5,368,051
[45] Date of Patent: Nov. 29, 1994

[54] METHOD OF REGENERATING ARTICULAR CARTILAGE

[76] Inventors: Allan R. Dunn; Susan L. Dunn, both of 1790 Sans Souci Blvd., North Miami, Fla. 33181

[21] Appl. No.: 85,554

[22] Filed: Jun. 30, 1993

[51] Int. Cl.⁵ .............................................. A61B 17/00
[52] U.S. Cl. .................................. 128/898; 424/426; 530/840
[58] Field of Search ............... 128/898; 424/422, 423, 424/426, 548; 623/16; 530/840

[56] References Cited

U.S. PATENT DOCUMENTS

| | | | |
|---|---|---|---|
| 5,041,138 | 8/1991 | Vacanti et al. | 623/16 |
| 5,206,023 | 4/1993 | Hunziker | 424/423 |

Primary Examiner—George Manuel
Attorney, Agent, or Firm—Malloy & Malloy

[57] ABSTRACT

A process for regenerating articular cartilage in a joint including the steps of exposing the joint having a cartilage defect, debriding the entire cartilage layer to the underlying bone-cartilage interface, to expose a plurality of vascular sinusoids in the sub-chondral layer of bone adjoining the joint surface, restoring the smooth contour and topography of the joint to its natural state, surgically closing the joints, and injecting a single dosage of a mixture of purified growth hormone and buffer solution into the joint so as to initiate the regenerative process, said mixture containing a quantity of purified growth hormone (somatotropin) which has been dissolved in a buffer solution.

17 Claims, 2 Drawing Sheets

METHOD OF REGENERATING ARTICULAR CARTILAGE

BACKGROUND OF THE INVENTION

1. Field of the Invention

The present invention relates to a process of regenerating articular cartilage surface which has been damaged, destroyed, or has otherwise become defective, thereby alleviating pain, stiffness, and other difficulties associated with a defective articular cartilage surface in a joint.

2. Description of the Related Art

Articular cartilage, the thin, fragile tissue layer covering the ends of bones, allows healthy joints to move freely and without pain. Many arthritic diseases and many degrees of trauma can, however, cause destruction or deterioration of this fragile layer, leading to pain, joint stiffness, and even crippling. From ancient times until the present, it has commonly been believed that this fragile surface, once lost, could never be restored. Attempts made in the past to regenerate or otherwise repair articular cartilage have been failures, thereby directing medical science to the development of substitutes and abandoning the potential for regeneration. Many substitutes have been developed to replace the articular cartilage joint surfaces, and these substitutes require implantations by surgery. Earlier substitutes included fascial transplants or transplants of entire joints such as the knee; however, the majority of these transplants were failures. More recently, medical science has developed implants which utilize metal and plastic components, but these are very costly because of the complicated implant components, the prolonged and repeated hospitalizations required for the surgical implantation of the components and the long periods of rehabilitation. In addition, many cases require one or more revision surgeries to replace defective, loose or infected implants. Most often, full motion and full activity are not achieved with the use of these implants. Further, the general discomfort associated with utilizing such implants makes an alternative method all the more desirable. The biological action of somatotropin acting in this process has been the subject of the applicant's research. The use of growth hormone in this manner is novel; heretofore, growth hormone has always been used clinically to enhance the growth of children with short stature. Somatotropin may have other effects on other organ systems but in the instant patent, the specific actions of somatotropin related cartilage growth which have been identified by Dunn's research are utilized herein. The major targets of somatotropin activity for cartilage regeneration are nests of stem (pleuripotential) cells in the marrow and the vascular system—specifically the vascular sinusoids located at the cartilage bone interface (sub-chondral bone) and the endothelial cells located therein.

The process of regeneration is biphasic. The initial phase, called Morphogenic Phase I, relies on the ability of growth hormone to stimulate proliferation of stem cells in the marrow, and the additional ability of somatotropin to form vascular glomular sinusoids 40' (Glomeruloids) from pre-existing single lumen vessels 40" in the sub-chondral bone. The second phase, the Generative Phase, involves the transfer of stem cells from the marrow to the Glomeruloids. Additional stem cells may be provided directly from the endothelial cells located in the vessel walls of the Glomeruloids. Within these Glomeruloids, the stem cells are transformed into cartilage cells first by transforming into prechondrocytes and then further transforming into chondrocytes. From the Glomeruloid layer, the chondrocytes pass upward and outward to form a new cartilage layer. The matrix of the cartilage layer is simultaneously produced by the new chondrocytes. The dosage of growth hormone to be applied in the single dosage is proportional to the body weight of the patient. The dosages were described above.

Heretofore, growth hormone has been used to augment the height of growth deficient children. The method of this invention relies on a novel use of growth hormone (somatotropin). There is no reliance on transplantation of tissue and thus all of the detrimental conditions of rejection, immune reaction, and failure are avoided. Until the present invention, growth hormone has never been used to regenerate tissue such as articular cartilage.

The method of the present invention is specifically adapted to initiate natural regeneration of articular cartilage on the joint surface through comparatively minor surgical procedures and the injection of one or more dosages of purified growth hormone (somatotropin) to initiate regeneration of and maintain the quality and quantity of articular cartilage. Accordingly, the method of the present invention provides a much needed improvement in the treatment and elimination of ailments associated with the deterioration or destruction of the articular cartilage surface of a joint.

SUMMARY OF THE INVENTION

The present invention is directed towards a method of regenerating articular cartilage in a joint separating two or more bones. Initially, the joint having a cartilage defect is surgically exposed. Once exposed, the cartilage layer of the joint is debrided and the surface is surgically restored to a smooth contour which closely approximates the original surface contour of that joint. For example, the cartilage layer is removed in order that a plurality of vascular sinusoids (Glomeruloids) at the cartilage-bone interface (sub-chondral bone) become exposed. Single lumen vessels are found in adults and glomerular sinusoids (or Glomeruloids) are found in immatures. Thus the term vascular structures or vascular units are generic terms applicable to adults and immatures. After the cartilage layer has been debrided, and the contour of the joint surface restored to a normal configuration, the joint is surgically closed. Next, a quantity of purified growth hormone is dissolved in a buffer solution at a specific range of Ph. The growth hormone dissolved in the buffer solution is then injected as a single loading dose into the joint cavity where it will initiate regeneration of articular cartilage along or at the joint surface.

It is a primary object of the present invention to provide a method which will provide natural regeneration of articular cartilage, thereby eliminating the necessity for transplants or artificial substitutes.

Still another object of the present invention is to provide a method of regenerating articular cartilage which will be effective in providing a new articular cartilage layer in a joint, thereby eliminating or substantially alleviating ailments associated with defective articular cartilage at joints.

A further object of the present invention is to provide a method of regenerating articular cartilage which will minimize the discomfort associated with loss or damage of the cartilage surface.

BRIEF DESCRIPTION OF THE DRAWINGS

For a fuller understanding of the nature of the present invention, reference should be made to the following detailed description made in connection with the accompanying drawings in which.

Like reference numerals refer to like parts throughout the several views of the drawings.

DETAILED DESCRIPTION OF THE PREFERRED EMBODIMENT

Figure 1:
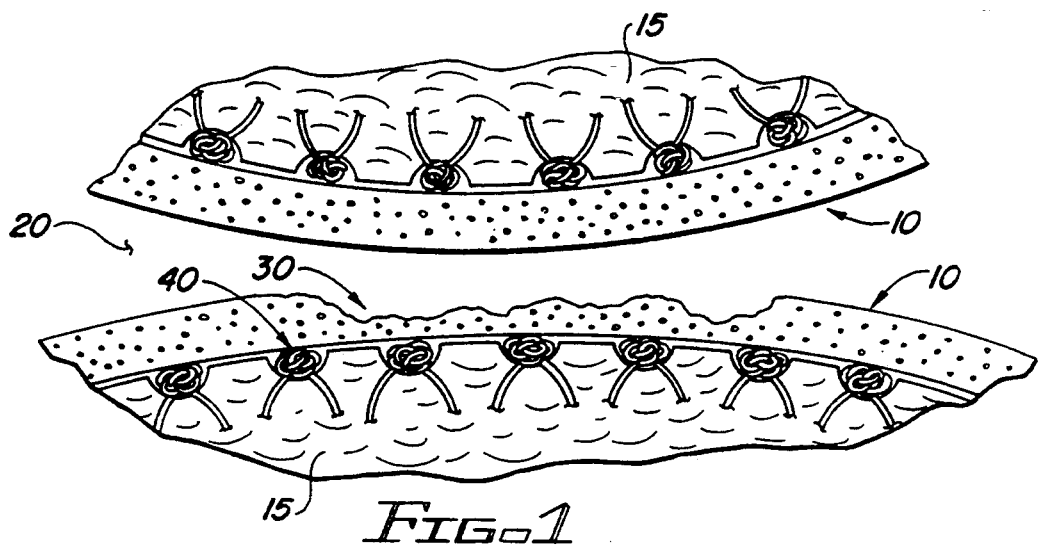
FIG. 1 is a cross-sectional view of a joint surface illustrating a deteriorated articular cartilage on the lower joint surface.

The present invention is directed specifically towards a method of regenerating articular cartilage 10. Articular cartilage 10, which is present between bones 15 at a joint 20 so as to provide a bearing type surface for facilitated movement between the bones 15. If articular cartilage is damaged or deteriorated this can result in significant pain, stiffness, discomfort, and even crippling to individuals suffering from a trauma or other ailments which destroy the joint surface. The articular cartilage 10 is a resilient layer of tissue which covers the ends of bones 15, and it has been traditionally assumed that once gone, it cannot be regrown or regenerated. The method of the present invention generally includes the steps of surgically exposing a joint 20 having a cartilage defect 30, removing the cartilage layer 10 of the joint so as to restore a smooth contour which closely approximates an original surface contour of the joint and to expose a plurality of vascular units (Glomeruloids) 40 or single lumen vessels 40″, see FIG. 3B, at the cartilage-bone interface, restoring the natural contours of the joint surfaces, surgically closing the joint, and injecting a solution of purified growth hormone dissolved in a buffer solution into the joint so as to regenerate the joint surface.

The method of the present invention is effective as a result of the discovery that in addition to the metaphyseal growth plate which exists near the ends of bones and which makes the bones grow during the maturing process, there is also an articular growth plate at the joint surface 45. The metaphyseal growth plate, once achieving full growth within the bone, ceases to function in an adult and disappears. The articular growth plate, however, remains intact, although growth-inactive, at the joint surface 10 in the adult. When exposed and properly stimulated by injecting purified growth hormones in the joint as in the method of the present invention, the articular growth plate will resume active growth. In addition under similar stimulation by purified growth hormone, the entire articular cartilage joint surface 10 can be regenerated.

Turning specifically to the method of the present invention, it is directed preferably for use on humans; however, it can be similarly effective with other animals so long as the necessary purified growth hormone is utilized. It is preferred that the growth hormone be species specific which means that human growth hormone would be used on humans and cattle growth hormone would be used on cattle, etc., for instance. When an articular cartilage defect is present in an individual, the joint 20 is first exposed so that the cartilage 10 may be accessed. Next, the cartilage layer 10 at the joint 20 is surgically debrided. This cartilage layer 10 can be removed utilizing various surgical scraping instruments such as curettes and burrs or scrapers 60 designed by Dunn.

Figures 5A, 5B, 5C:
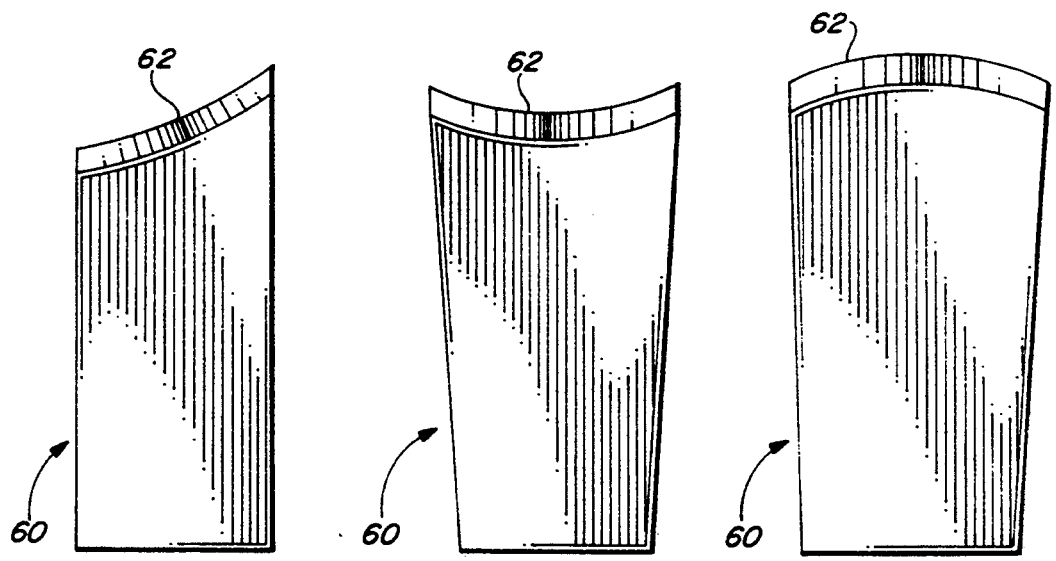
FIGS. 5A, 5B, and 5C are perspective views of the sharpened scrapers to be utilized in the method of the present invention.

These scrapers 60 are designed as templates which mirror the natural contours of the joint surfaces 45. One edge 62 of the scraper is sharpened (FIG. 5). It is the sharpened edge 62 that is used to restore the original contour. The primary objective is to restore a smooth contour to the joint surface 45 and to expose a plurality of vascular units Glomeruloids 40 (or single lumen vessel 40″) at the sub-chondral layer. With regard to the necessity for a smooth contour, further surgical contouring is performed to achieve the desired contour. It is preferred that the contour also closely approximate the original surface contour of that joint so it will function to provide normal movement and to be more comfortable and more natural. It is highly preferred that all of the articular cartilage 10 present be removed so that the regeneration can take effect along the entire joint surface, thereby providing a more uniform regenerated surface. The second important purpose of removing the cartilage layer is to expose a plurality of vascular units (Glomeruloids) 40 or single lumen vessels 40 present at the cartilage bone interface.

Figure 3A:
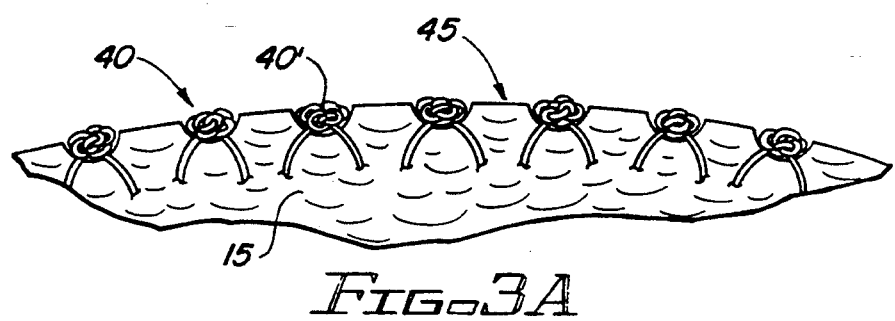
FIG. 3A is an isolated cross-sectional view illustrating the exposed vascular units at the sub-chondral layer with intact Glomeruloids composed of multiple curved blood vessels.
Figure 3B:
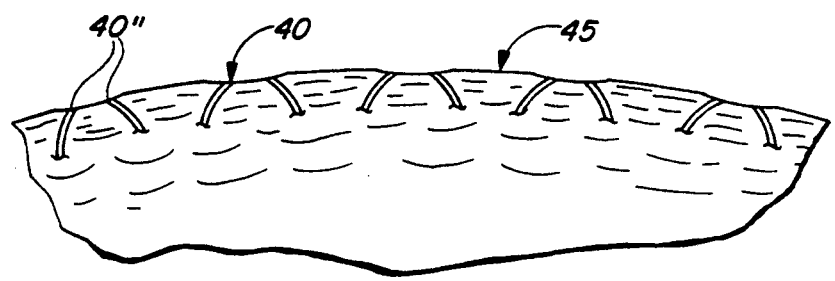
FIG. 3B is an isolated cross-sectional view illustrating the exposed vascular units at the sub-chondral layer following deep debridement leaving only single lumen blood vessels.

As illustrated in FIGS. 3A and 3B, the exposed vascular units 40 may preferably include a number of glomerular organelles 40′ composed of multiple curved blood vessels as in FIG. 3A or single lumen vessels 40″, as in FIG. 3B. These individual glomerular organelles 40′, however may become damaged, either during movement of the joint surface or during removal of the cartilage layer 10. Accordingly, it can be equally effected to remove sufficiently the cartilage layer 10 and also a portion of the underlying bone 15 so as to expose the number of single lumen blood vessels 40″, as illustrated in FIG. 3B. Through use of the growth hormone the single lumen vessels 40″, will be transformed into Glomeruloids 40 by a morphogenic action (Phase I) of growth hormone which was described previously.

Figure 4:
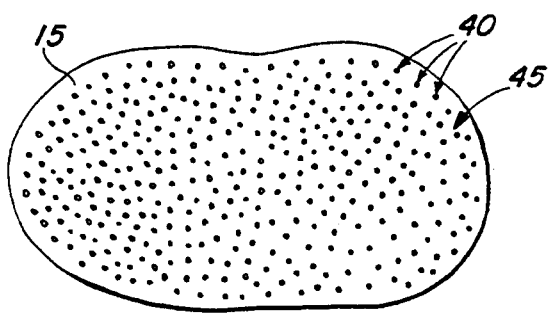
FIG. 4 is a top view of the debrided joint surface illustrating a plurality of fine bleeding points which indicate the presence of exposed vascular units at the sub-chondral layer of bone.

As illustrated in FIG. 4, once the joint surface is appropriately debrided, a plurality of punctate bleeding points is visible on the joint surface 45, these bleeding points being a result of the visibility of the sinusoidal layer of bone and the individual vascular units 40 emerging therein, the vascular units 40 often resulting in points of blood at their point of exposure. It is of particular importance to expose the vascular units 40 in the regenerative process.

Generally, marrow within the body produces pleuripotential cells, a form of germinal cell, which become introduced into the bloodstream. These pleuripotential cells arrive at the sinusoidal layer of the bone through the vascular units 40 (glomeruloids) where necessary reaction can take place. Once the vascular units 40 are exposed, it is preferable to lavage the joint utilizing sterile saline buffer solution to remove all debris. Cartilage particles and debris have the potential to grow over a prolonged period of time to form loose bodies and therefore must be removed. Such loose body will damage the surface and impede motion of the joint. It is preferred that the sterile saline solution utilized should have a Ph in the range of 8.0 to 8.3. After the joint is lavaged, the joint is then surgically closed. Next, a quantity of purified growth hormone must be dissolved in a buffer solution.

It is preferred that the growth hormone (Somatotropin) utilized be species specific and be identical to naturally produced growth hormones of that species. If a biologically engineered hormone alternative be used, it must have an amino acid sequence identical to the natural hormone. It is preferential that the growth hormone be biologically engineered to exactly duplicate the natural hormone and to assure maximum purity, and avoid the possibility of transmitting disease. If the growth hormone is to be prepared from pituitary glands retrieved from cadavers, the hormone preparation may transmit rare forms of neurological disease even though it may be highly purified.

Figure 2:
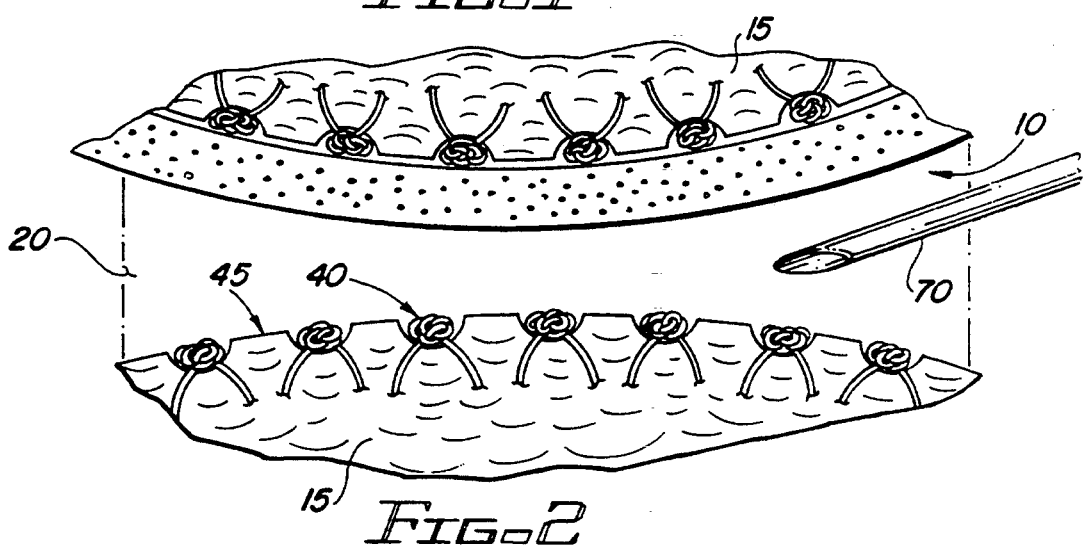
FIG. 2 is an isolated view illustrating the application of growth hormone and buffer solution in the joint cavity where it coats all the Glomeruloids or single unit vessels. The lower surface has been debrided of cartilage to expose the sub-chondral bone and whole Glomeruloids.

The purified growth hormone powder is to be dissolved in a buffer solution for injection. Preferably, the buffer solution is Hank's Buffer Solution having a range of Ph between 8.0 and 8.3. Generally, buffer solutions have pH's of approximately 7.0 to 7.4 which is the range of biological Ph. However, to properly dissolve the growth hormone in the buffer solution, it is preferred that the buffer solution have the higher Ph range of between 8.0 and 8.3. Other preparations of purified growth hormone may, due to their chemical composition, require buffer solutions of other ranges of Ph. The growth hormone will be dissolved in the buffer solution at a preferred dosage of 1.0 to 1.50 milligrams of growth hormone per milliliter of buffer solution. An individual dosage to be administered is related to the animal's weight, but will be in the preferred range of 0.25 milligrams to 0.75 milligrams per Kilogram of body weight. The Ph is not adjusted to the physiological range (7.0 to 7.4) at this point. Once the growth hormone and buffer solution have been mixed, a single dosage of the mixture is injected to the joint, as illustrated in FIG. 2. The growth hormone is injected, utilizing a syringe 70, into the joint space 20 and not directly into the bone 15 or other tissue. In this manner, it may flow over the entire joint surface 45 and react with all vascular units 40 exposed at the bone surface. A portion of the purified growth hormone will be absorbed into the bloodstream after four hours. One of the systemic effects associated with this absorption into the general circulation will be to stimulate production of stem cells in the marrow. The growth hormone will react to attract pleuripotential cells to the sinusoidal layer of the bone, the pleuripotential cells being present through the vascular units. This will initiate cell layer growth at the sub-chondral layer, and eventually produce enough cartilage to form a new joint surface. Accordingly, a new layer of articular cartilage 10 is formed through a patient's normal growth potentials without relying on transplantation of tissues with all of its associated problems. Depending on the individual patient's condition, repeated, periodical injections of the growth hormone may be required. This is especially necessary in situations where a patient suffers from a disease which will continuously impair or destroy the cartilage surface, or antagonize the action of the growth hormone.

Although the method of the present invention has heretofore been described as including a surgical procedure to expose a joint having a cartilage defect, it will be appreciated that the present invention does not require surgical exposure of the joint in order to achieve a therapeutic effect upon the articular cartilage therein from the intra-articular injection of purified growth hormone. Accordingly, the method of the present invention also comprises the intra-articular injection of a purified growth hormone dissolved in buffer solution into a joint that has not undergone the above-described surgical procedure, to produce additional articular cartilage surface thickness, to improve the quantity and quality of existing cartilage, and to produce additional crystal clear joint fluid which may be useful to improve the quality of the cartilage and to provide additional lubrication to the joint surfaces.

Now that the invention has been described,
What is claimed is:

1. A method of regenerating articular cartilage comprising the steps of:
   a) surgically exposing a joint having a cartilage defect,
   b) exposing a plurality of vascular units at a sinusoidal layer of bone along the joint surface,
   c) removing the cartilage layer at the joint so as to restore a smooth contour
   d) further surgically contouring the joint surface to restore the natural contour of the joint,
   e) surgically lavaging the joint to remove all cartilage and bone particles and debris,
   f) surgically closing said joint,
   g) dissolving a quantity of purified growth hormone in a buffer solution, and
   h) injecting a single dosage of said growth hormone and said buffer solution into said joint so as to initiate regeneration along the joint surface.

2. A method of regenerating articular cartilage as recited in claim 1 wherein said buffer solution is Hank's Buffer Solution having a range of Ph between 8.0 and 8.3.

3. A method of regenerating articular cartilage as recited in claim 2 wherein said growth hormone is species specific so as to be identical to naturally produced growth hormones.

4. A method of regenerating articular cartilage as recited in claim 3 wherein said growth hormone is biologically engineered to assure maximum purity and disease elimination.

5. A method of regenerating articular cartilage as recited in claim 4 wherein said joint is lavaged utilizing sterile saline solution having a Ph in the range of 8.0 to 8.3 prior to surgically closing said joint.

6. A method of regenerating articular cartilage as recited in claim 5 where a range of about 1.0 to 1.5 milligrams of said purified growth hormone is dissolved in 1 milliliter of said buffer solution, the total volume of said dosage being dependent upon the weight of the individual subject being injected.

7. A method of regenerating articular cartilage as recited in claim 6 wherein said single dosage is about 0.25 to 0.75 milligrams of purified growth hormone per Kilogram of body weight.

8. A method of regenerating articular cartilage as recited in claim 7 wherein repeated, periodic injections of said growth hormone and said buffer solution are made to create and maintain the required amounts of the cartilage.

9. A method of regenerating articular cartilage as recited in claim 1 wherein said vascular units include single lumen blood vessels to be transformed by said growth hormone into glomerular organelles of multiple curved vessels (Glomeruloids).

10. A method of regenerating articular cartilage as recited in claim 1 wherein said vascular units includes glomerular organelles composed of multiple curved vessels.

11. A method of regenerating articular cartilage as recited in claim 10 wherein a lavage with saline during the debridement to prevent cell necrosis which may be caused by friction, heat, or drying of the tissue and cells.

12. A method of producing additional articular cartilage surface thickness, improving the quality and quantity of the existing cartilage, and producing additional crystal clear joint fluid in an individual subject, comprising the steps of dissolving a predetermined quantity of purified growth hormone in a buffer solution, and injecting at least one dosage of said growth hormone and said buffer solution intra-articularly into a joint.

13. A method as recited in claim 12 wherein said dissolving step comprises dissolving said purified growth hormone in a buffer solution comprising Hank's Buffer Solution having a range of pH between 8.0 and 8.3.

14. A method as recited in claim 12 wherein said dissolving step comprises dissolving a growth hormone that is species specific so as to be identical to naturally produced growth hormone.

15. A method as recited in claim 12 wherein said dissolving step comprises dissolving a range of about 1.0 to 1.5 milligrams of said purified growth hormone in 1 milliliter of said buffer solution, the total volume of said dosage being dependent upon the weight of the individual subject being injected.

16. A method as recited in claim 12 wherein said dissolving step comprises dissolving about 0.25 to 0.75 milligrams of said purified growth hormone per kilogram of body weight in 1 milliliter of said buffer solution to form a single dosage.

17. A method of regenerating articular cartilage as recited in claim 14 wherein said injecting step comprises repeated, periodic injections of said growth hormone and said buffer solution into said joint.

* * * * *